(12) United States Patent
Skeps et al.

(10) Patent No.: US 7,027,934 B2
(45) Date of Patent: Apr. 11, 2006

(54) APPARATUS AND METHOD FOR AUTOMATED WEB INSPECTION

(75) Inventors: Carl J. Skeps, Lakeville, MN (US); James A. Masterman, Lake Elmo, MN (US); Steven P. Floeder, Shoreview, MN (US); Brandon T. Berg, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 36 days.

(21) Appl. No.: 10/669,197

(22) Filed: Sep. 24, 2003

(65) Prior Publication Data

US 2005/0075801 A1  Apr. 7, 2005

(51) Int. Cl.
*G01B 5/28* (2006.01)
*G06K 9/00* (2006.01)

(52) U.S. Cl. ............................ 702/35; 702/36; 382/149

(58) Field of Classification Search ................ 702/35, 702/36; 382/149, 141, 306, 305; 348/88, 348/125; 356/429, 430; 358/429, 430
See application file for complete search history.

(56) References Cited

U.S. PATENT DOCUMENTS

| 4,173,441 | A | * | 11/1979 | Wolf ......................... 356/431 |
| 5,544,256 | A | | 8/1996 | Brecher et al. |
| 6,092,059 | A | | 7/2000 | Straforini et al. |
| 6,100,989 | A | | 8/2000 | Leuenberger |
| 6,259,109 | B1 | * | 7/2001 | Dalmia et al. ......... 250/559.08 |
| 6,266,436 | B1 | | 7/2001 | Bett et al. |
| 6,266,437 | B1 | * | 7/2001 | Eichel et al. ............... 382/149 |
| 6,330,350 | B1 | | 12/2001 | Ahn et al. |
| 6,404,910 | B1 | | 6/2002 | Ungpiyakul et al. |
| 6,407,373 | B1 | | 6/2002 | Dotan |
| 6,484,306 | B1 | | 11/2002 | Bokor et al. |
| 6,496,596 | B1 | | 12/2002 | Zika et al. |
| 6,778,694 | B1 | | 8/2004 | Alexandre |
| 2002/0039436 | A1 | | 4/2002 | Alumot et al. |
| 2002/0080347 | A1 | | 6/2002 | Yoda et al. |
| 2002/0110269 | A1 | * | 8/2002 | Floeder et al. ............. 382/141 |

FOREIGN PATENT DOCUMENTS

| JP | 62 093637 | 4/1987 |
| JP | 11 248641 | 9/1999 |
| JP | 2000 009447 | 1/2000 |
| WO | WO 02/21105 | 3/2002 |
| WO | WO 02/065107 A2 | 8/2002 |

OTHER PUBLICATIONS

Wenyuan Xu et al., "Industrial Web Inspection for Manufacturing Process Understanding and Control", Proceedings of the SPIE—The International Society for Optical engineering SPIE-INT. Soc. Opt. Eng USA, vol. 3652, Jan. 1, 1999 pp. 10-20, XP002307220, ISSN: 0277-786X, Figure 1.

* cited by examiner

*Primary Examiner*—John Barlow
*Assistant Examiner*—Meagan S Walling

(57) ABSTRACT

A method of inspecting a moving web. The method includes imaging a sequential portion of the continuously moving web to provide digital information. The digital information is then processed with an initial algorithm to identify any regions on the web containing anomalies. Image information corresponding to any identified region within the digital information is then selected. The selected image information is then analyzed with at least one subsequent algorithm to distinguish actual defects from among the anomalies.

15 Claims, 4 Drawing Sheets

APPARATUS AND METHOD FOR AUTOMATED WEB INSPECTION

TECHNICAL FIELD

The present invention relates to automated inspection systems, and more particularly to a system and device for optically inspecting continuously moving webs.

BACKGROUND

Inspection systems for the analysis of moving web materials have proven critical to modem manufacturing operations. Industries as varied as metal fabrication, paper, nonwovens, and films rely on these inspection systems for both product certification and online process monitoring. One major difficulty in the industry is related to the extremely high data processing rates required to keep up with current manufacturing processes. With webs of commercially viable width and web speeds that are typically used and pixel sizes that are typically needed, data acquisition speeds of tens or even hundreds of megabytes per second are required of the inspection systems. It is a continual challenge to process images and perform accurate defect detection at these data rates.

The art has responded to this dilemma by limiting the image processing to very simple algorithms, by limiting the scope and complexity of the detection algorithms, and by using custom inspection system architectures incorporating custom electronic hardware or dedicated preprocessors, each working on part of the data stream. While such systems are capable of achieving the data rates required for the inspection of moving webs, is very difficult to adapt the system for a new production process and web materials. Also, processing algorithms are limited to the capabilities of dedicated processing modules. Finally, as the image processing algorithms become more complex, the hardware required to implement the required processing quickly becomes unmanageable.

The manufacturing industry has recognized the importance of being able to produce product "just-in-time" with obvious advantages in reduced inventory. However, achieving this goal often has manufacturers working to develop systems and devices that allow a rapid change over between various products. The rapid changeover between products is inconsistent with the specialized signal processing hardware the art of optical inspection of moving webs now requires.

Another dilemma occurs in situations when a given product can be later used for multiple applications, with each of the multiple applications requiring different quality levels. The difficulty is that during the time of manufacture, it is not known which quality level will be required. Therefore, the current art attempts to grade quality level after defect detection by using various defect classification techniques based on spatial features of the extracted defects. While this is sometimes adequate when gross differences exist between defect levels for different quality requirements, it is not adequate for more demanding situations in which more subtle differences between defects require different image processing and defect extraction algorithms. Thus, if one waits until after defect extraction for classification, information is lost and the classification is impossible.

SUMMARY OF THE INVENTION

The present invention provides a system for the inspection of moving webs. It solves the difficulties described above through the use of unique application specific defect detection methods. This inventive method provides greatly enhanced defect detection capability at little or no cost in terms of defect processing time or resources, thereby allowing the inspection system to keep up with the demanding data processing rates needed in web inspection applications. It also allows one to save all information for every anomaly for use at a later time, thereby providing deferred defect detection depending on quality levels required for the final product application.

The inspection system acquires information about the web from an optical device and performs a preliminary examination with a first, typically less sophisticated algorithm. Image information about the regions of the web containing anomalies is selected, accepting the likelihood that some of the anomalies will be defective, but many could be "false positives", anomalies that are not defective. In fact, some areas may be defective if the product is used in a particular application, but not defective if it is used in another. To effectively separate actual defects from anomalies, the original image information is reconsidered later and subjected to at least one of a variety of more sophisticated image processing and defect extraction algorithms.

It is an advantage of this invention that this reconsideration of the original image information can be performed at a convenient time, even after the inspected web has been wound onto a roll and is unavailable. A related advantage is that the speed of the moving web during the inspection can be much greater than is possible when the entire surface of the web is subjected to a sophisticated analysis.

While the present invention is particularly useful with normally unpatterned webs, it is also contemplated that the method is applicable to normally patterned webs. When a normally patterned web is being subjected to the present process, the initial algorithm used to process the digital information must be sufficient to distinguish between regions of the web containing perfect pattern from regions of the web containing pattern and also possible defects. Data reduction, so that only some fraction of the digital information needs to be extracted and subjected to the subsequent algorithm, is the goal.

More particularly, one embodiment of the invention can be thought of as a method of inspecting a moving web. The method includes imaging a sequential portion of the continuously moving web to provide digital information. The digital information is then processed with an initial algorithm to identify any regions on the web containing anomalies. Image information corresponding to any identified region within the digital information is then selected. The selected image information is then analyzed with at least one subsequent algorithm to distinguish actual defects from among the anomalies.

In many preferred embodiments, it is convenient to store or buffer the selected image information prior to analyzing it. Indeed, it is often convenient to retain the stored or buffered information for a time and perform the analysis only after the imaging has been performed on the entire web.

Various image processing techniques can be used for the initial algorithm, but algorithms comprising the steps of thresholding the digital information and forming a blob list have been found to be particularly convenient because they can be performed with very small computational cost. Depending on the exact nature of the web being inspected, the invention can be used with reflected, transmitted, or transflected light. The invention is useful with either a single or multiple imaging sources.

Other features and advantages will be apparent from the following description of the embodiments thereof, and from the claims.

DEFINITIONS

For purposes of the present invention, the following terms used in this application are nndefined as follows:

"web" means a sheet of material having a fixed dimension in one direction and either a predetermined or indeterminate length in the orthogonal direction;

"sequential" means that an image is formed by a succession of single lines, or areas of the web that optically maps to a single row of sensor elements (pixels);

"pixel" means a picture element represented by one or more digital values;

"blob" means a connected set of pixels in a binary image;

"defect" means an undesirable occurrence in a product;

"anomaly" or "anomalies" mean a deviation from normal product that may or may not be a defect, depending on its characteristics and severity.

"gray scale" means pixels having a multitude of possible values, e.g. 256 digital values;

"binarization" is an operation for transforming a pixel into a binary value;

"filter" is a mathematical transformation of an input image to a desired output image, filters are typically used to enhance contrast of a desired property within an image; and "application specific" means defining product requirements based on its intended use.

BRIEF DESCRIPTION OF THE DRAWINGS

In the several figures of the attached drawing, like parts bear like reference numerals, and.

DETAILED DESCRIPTION

Figure 1:
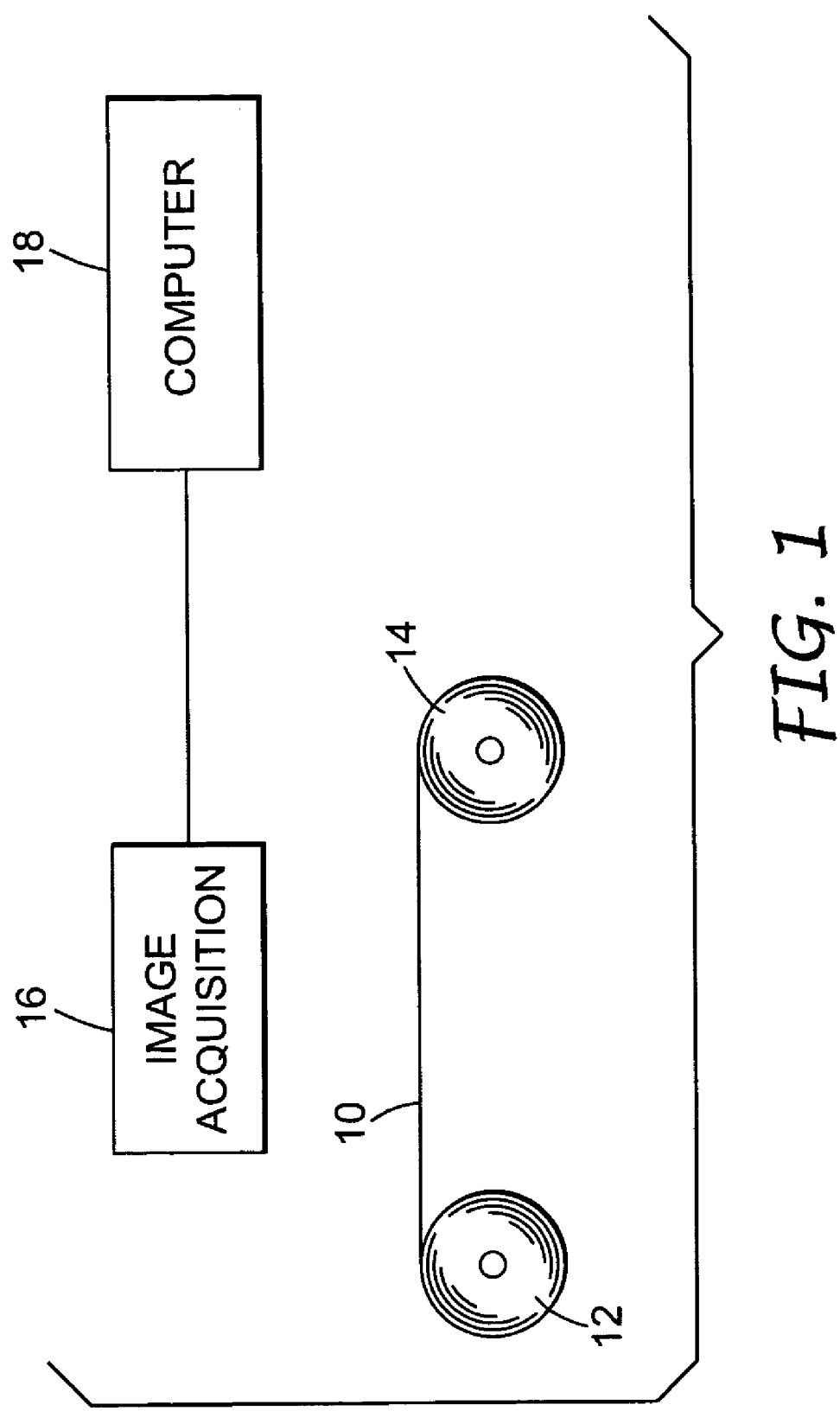
FIG. 1 illustrates a schematic view of an exemplary inspection apparatus according to the present invention.

The present invention is a method for optically inspecting a continuous moving web. FIG. 1 is a diagram depicting one way in which the method of the present invention may be carried out. A segment of a continuously moving web 10 is positioned between two support rolls 12, 14. An image acquisition device 16 is positioned in close proximity to the continuously moving web 10. The image acquisition device 16 scans a sequential portion of the continuously moving web 10 to obtain data about the respective sequential portion. The data is transmitted to a computer 18 that collects and analyzes the data. The digital information is then processed with an initial algorithm to identify any regions on the web containing anomalies. Image information corresponding to any anomaly within the digital information is then selected. The selected image information is then analyzed with at least one subsequent algorithm to distinguish actual defects from among the anomalies.

Web Materials

In accordance with the present invention, the web may include any sheet-like material having a fixed dimension in one direction and either a predetermined or indeterminate length in the orthogonal direction. The invention is preferably suited to deal with webs that are continuously moving. Materials provided in web form that may be optically imaged are suitable for use with the present invention. Examples of web materials include, but are not limited to metals, paper, wovens, non-wovens, glass, polymeric films or combinations thereof. Metals may include such materials as steel or aluminum. Wovens generally include various fabrics. Non-wovens include materials, such as paper, filter media, or insulating material. Films include, for example, clear and opaque polymeric films including laminates and coated films.

One type of inspection problem particularly suitable to resolution through use of the present invention is the inspection of optical films. With films intended for use in optical applications such as the surface of a computer display, subtle defects can loom large to a user who is looking at the display for hours at a time. Sometimes defining exactly what sort of defect in this sort of application will be unacceptably burdensome to the user, and what sort of defect is harmless is quite complex. A scheme for reducing the complexity of the determination is presented with more particularity below.

A second type of inspection problem is the inspection of flexible circuit webs. The invention is particularly suited for dealing with the complexity involved where individual circuits on a flexible circuit web have repeating circuit patterns deposited or formed on a flexible substrate. A web typically has multiple individual circuits each including various small parts arranged in arbitrary patterns. The individual circuits are later separated from the web by e.g. die cutting for use in discrete electrical applications.

For many applications suited for the present invention, the web materials or combined materials may preferably have an applied coating. Coatings that may be optically imaged are suitable for use with the present invention. The coatings are generally applied to an exposed surface of the base web material. Examples of coatings include adhesives, optical density coatings, low adhesion backside coatings, metalized coatings, optically active coatings, electrically conductive or nonconductive coatings, or combinations thereof. The coating may be applied to at least a portion of the web material or may fully cover a surface of the base web material.

Image Acquisition

The acquisition of the image is accomplished through the use of conventional imaging devices that are capable of reading a sequential portion of the moving web and providing output in the form of a digital data stream. For purposes of the invention, the imaging device may include a camera that directly provides a digital data stream or an analog camera with an additional analog to digital converter. Furthermore, other sensors, such as, for example, laser scanners may be utilized as the imaging device. A sequential portion of the web indicates that the data is acquired by a succession of single lines. Single lines comprise an area of the continuously moving web that optically map to a single row of sensor elements or pixels. Examples of devices suitable for acquiring the image include linescan cameras such as Model#LD21 from Perkin Elmer (Sunnyvale, Calif.), Piranha Models from Dalsa (Waterloo, Ontario, Canada), or Model#TH78H15 from Thompson-CSF (Totawa, N.J.). Additional examples include laser scanners from Surface Inspection Systems GmbH (Munich, Germany) in conjunction with an analog to digital converter.

The image may be optionally acquired through the utilization of optic assemblies that assist in the procurement of the image. The assemblies may be either part of a camera, or may be separate from the camera. Optic assemblies utilize reflected light, transmitted light, or transflected light during the imaging process. Reflected light is suitable for the detection of defects caused by web surface deformations such as surface scratches.

Analysis of Digital Information

Figure 2:
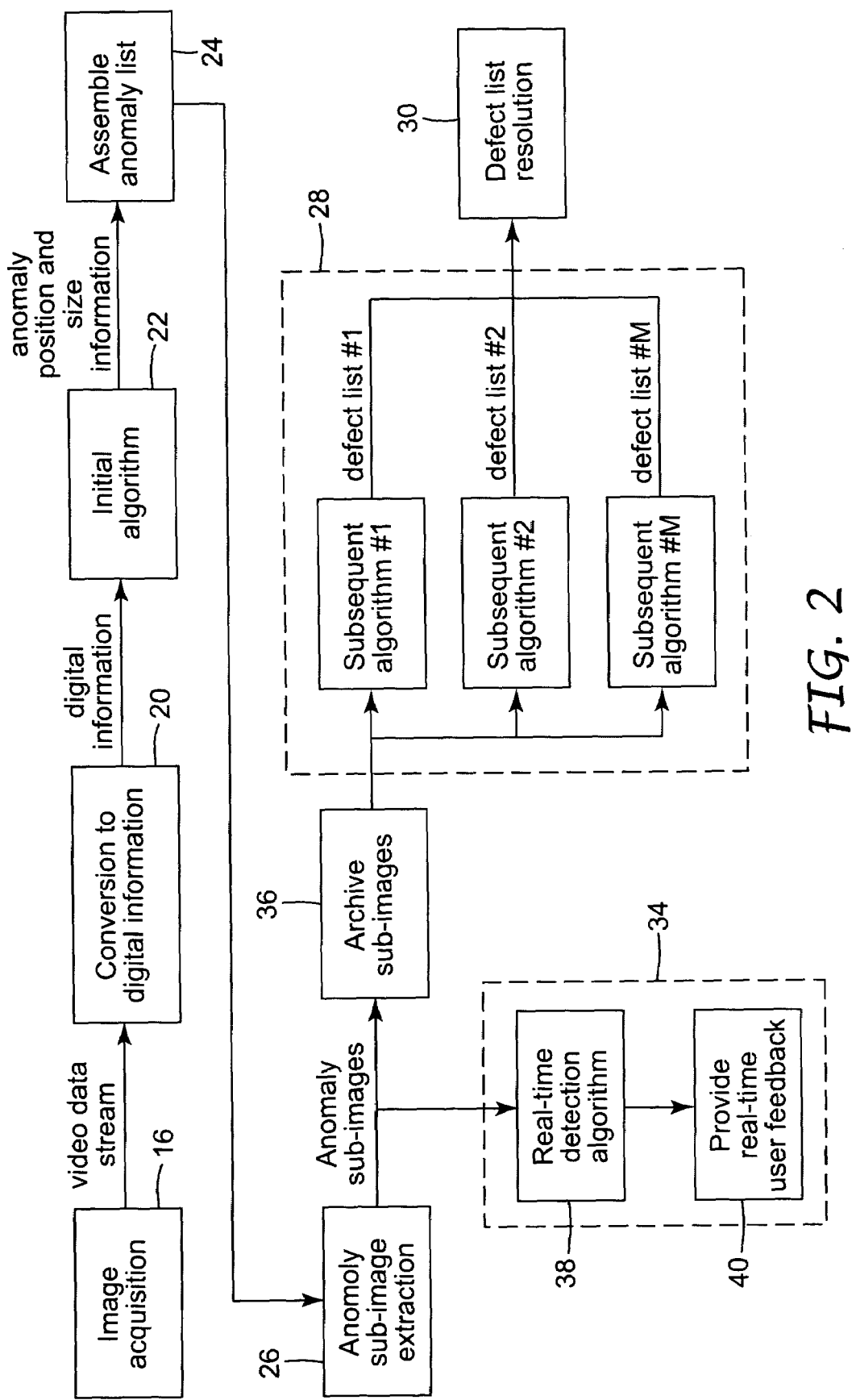
FIG. 2 illustrates a flowchart of an exemplary method according to the present invention.

FIG. 2 is a flowchart of an exemplary method according to the present invention. Information from the image acquisition device 16 is converted in step 20 to provide digital information. The digital information is subjected to an initial algorithm 22 to identify regions of the web containing anomalies. In convenient embodiments, the initial algorithm 22 is very fast so as to be capable of being performed in real time by general purpose computing equipment even if the line speed of the moving web is great. This is usually true in most embodiments of the invention, even if the sophistication of the algorithm is such that the identified regions containing anomalies include many "false positives." Even though there may be many false positives, the initial algorithm is preferably designed such that escapes, true defects not detected as anomalies, rarely, if ever occur.

It is usually convenient to perform the step 24 of assembling information about the identified regions containing anomalies into a list. The list conveniently includes the start position and encompassing pixel area of each identified region. This list and the original digital information are used to perform the step 26 of extracting the identified regions containing anomalies from the digital information. Data reduction, so that only some fraction of the digital information needs to be extracted for further, more sophisticated analysis is a preferred result of the invention. In preferred embodiments, the identified regions contain information, as indicated by size in any convenient measure such as file size in bytes, at least an order of magnitude less than the digital information. In application, the present invention has demonstrated actual data reduction in an order of magnitude of between 3 and 8.

The extracted anomaly images may be optionally stored in a database 36 for later analysis or may be transferred directly for processing by multiple detection algorithms 28. If the images are stored, they can be analyzed at a later time. It may be as soon as several milliseconds for immediate feedback to the product making operation or as long as several weeks later for analysis at remote converting operations after determining the product application based on, for example, current customer orders. The preferred embodiment is to store images in a real-time database for enough time to perform all of the subsequent detection algorithms required for any possible product final product use.

The extracted anomalies are then analyzed with at least one subsequent detection algorithm 28 to determine which anomalies represent actual defects in the moving web 10. In the flowchart of FIG. 2, "M" different subsequent algorithms are in use. In many preferred embodiments, a larger number of rather simpler algorithms are conveniently used in parallel. In particular, it is often convenient that at least one of the subsequent algorithms includes comparing each anomaly against a combination threshold-pixel size criterion. In actual practice with e.g. optical films, an anomaly having only a subtle difference in brightness value from a target is unacceptable if the area is large, and an anomaly having a great difference in brightness from a target value is unacceptable even if the area is very small. However, the detection algorithms can incorporate very complex image processing and defect extraction including, but not limited to, neighborhood averaging, neighborhood ranking, contrast expansion, various monadic and dyadic image manipulations, digital filtering such as Laplacian filters, Sobel operators, high-pass filtering and low-pass filtering, texture analysis, fractal analysis, frequency processing such as Fourier transforms and wavelet transforms, convolutions, morphological processing, thresholding, connected component analyses, blob processing, blob classifications, or combinations thereof. The individual results from the M subsequent processing algorithm are then subjected to a defect list resolution process 30 to form a composite defect list. The simplest defect resolution process, a simple OR logic, serves in many preferred embodiments.

The algorithms employed in the present invention include those conventionally utilized in the field of web inspection. Combinations of the algorithms may be used for either the first or subsequent algorithms. Those skilled in the art of establishing web inspection systems are cable of matching one or more algorithms with specific web and defect types to achieve a desired accuracy level of defect detection.

The results from the anomaly sub-image extraction 26 may provide some benefit for real time feedback 34 of the web manufacturing process. However, in practice, it may be convenient to run an additional real time detection algorithm 38 that is sufficient to identify patterns in the anomalies indicative of a process fault of the sort an operator could ameliorate with direct intervention. To be useful for this purpose, the identified patterns are communicated to the operator as real-time feedback 40.

Figure 3:
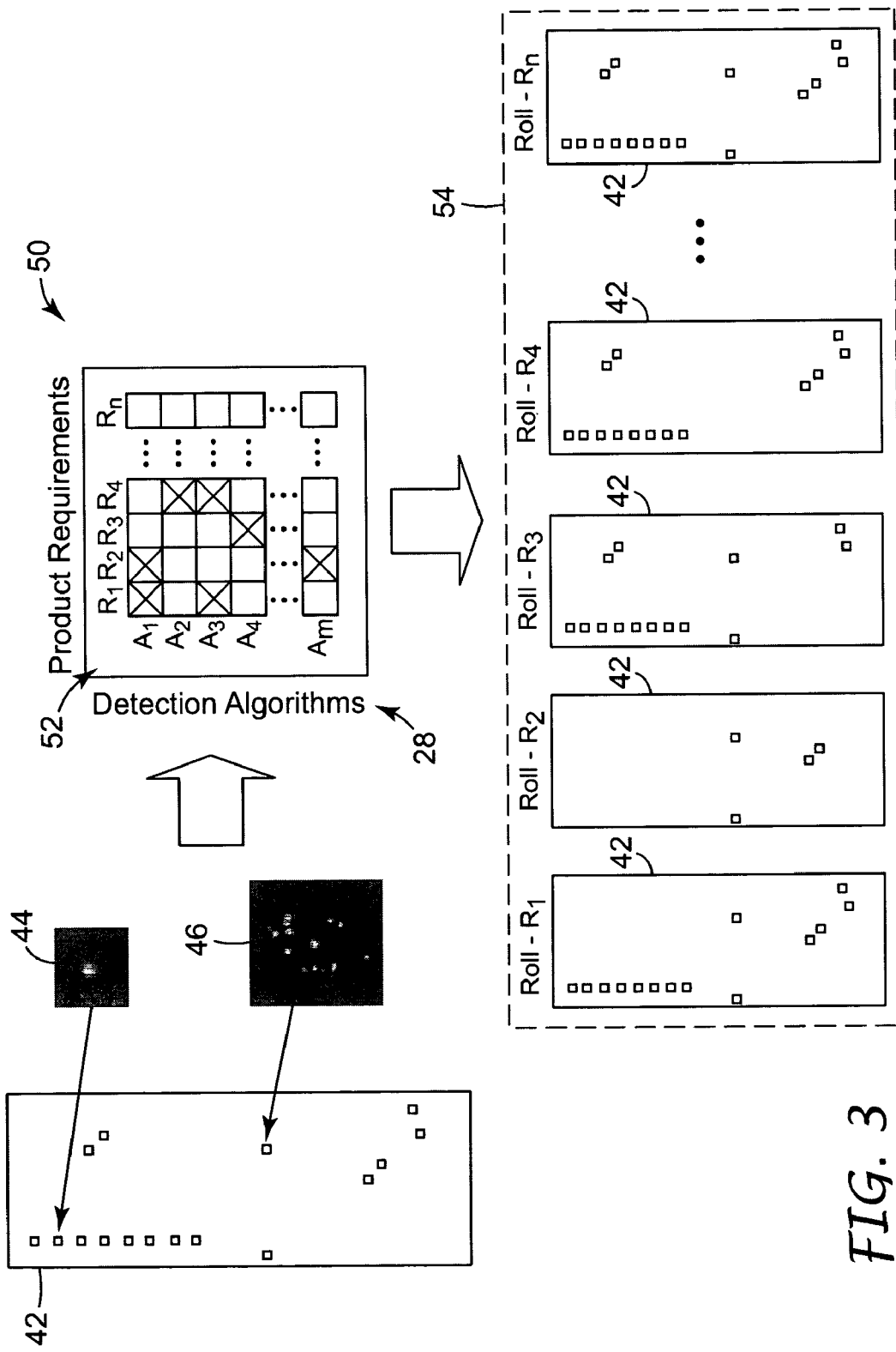
FIG. 3 illustrates application specific processing concept in accordance with the present invention.

FIG. 3 shows a preferred embodiment of the application specific detection incorporating multiple defect detection algorithms required for different product requirements. First, a roll 42 is imaged and anomaly images, such as images 44, 46, are extracted using a simple first detection algorithm, not shown. Then each anomaly image is processed using up to M detection algorithms 28 as needed for up to N different product requirements 50. The step 30 (in FIG. 2) of resolving the defect list is conveniently accomplished by the use of a cross-reference table 52. The exemplary cross-reference table 52 shows which detection algorithms 28 are considered in determining whether each anomaly is a defect or a false positive for a given product requirement 50. For example, a given piece of film could finally be used in three different applications; the first having very stringent quality requirements, the second having moderate requirements, and the third have minimal requirements. Depending on the defect distribution in the roll and the upcoming product orders, the given roll may produce more optimal converting results if it is converted and used for one product application rather than another.

Referring again to FIG. 3, each of the N product requirements can be accomplished using selected combinations of individual defect processing algorithms. The algorithms may use very simple threshold and minimum blob processing or more complex algorithms such as spatial filters, morphological operations, frequency filters, wavelet processing, or any other known image processing algorithms. In this exemplary cross-reference table 52, product requirement $R_1$ uses a combination of algorithms $A_2$, $A_4$, and $A_M$, each applied to every anomaly image to determine which anomalies are actual defects for $R_1$. In most convenient embodiments, a simple OR logic is employed, i.e. if any of $A_2$, $A_4$, and $A_M$ report the anomaly as an actual defect, that portion of roll 42 does not satisfy product requirement $R_1$. For specialized applications, the logic through which the reports of the subsequent algorithms 28 are combined into a determination of whether a product requirement 50 is satisfied may be more complex than a simple OR logic. Similarly, product requirement $R_2$ uses $A_2$, $A_3$, and $A_4$, etc. Thus, the anomalies that are identified as defects for $R_2$ may be similar to or significantly different than defects for $R_1$.

After determining which anomalies are considered actual defects by using cross-reference table 52, it may be convenient to draw one or more (up to N) different maps 54 of actual defect locations corresponding to the various product requirements for the roll 42. Once this has been done, it is often possible to discard the subimage information to minimize the needed storage media.

Because this invention is computationally efficient, a preferred embodiment utilizes computational processing units to provide both the initial algorithm processing and subimage extraction, as well as subsequent processing of subimages with additional detection algorithms. Also, the invention is not limited to a single imaging device, but may be implemented with an arbitrary number of imaging devices. In that case, a single computational processing unit may be used for each imaging device, or multiple imaging devices can be handled by a single computational processing unit for realtime processing using the initial algorithm. One or more computational processing units may then be applied to subsequent processing algorithms. Workstations, servers, personal computers, or other general purpose computers are preferred embodiments for computational processing units. However, other implementations using digital signal processors, single board computers, transputers, embedded electronic hardware, or combinations thereof are applicable.

A simple but representative example showing advantages of this invention is described in this section. This illustrates a feature of many optical type films. Subtle anomalies are considered defective only if they are large while even very small anomalies can be defective if they have high contrast. In this case, anomalies that have greater deviation from the background image level have high contrast.

Figure 4A:
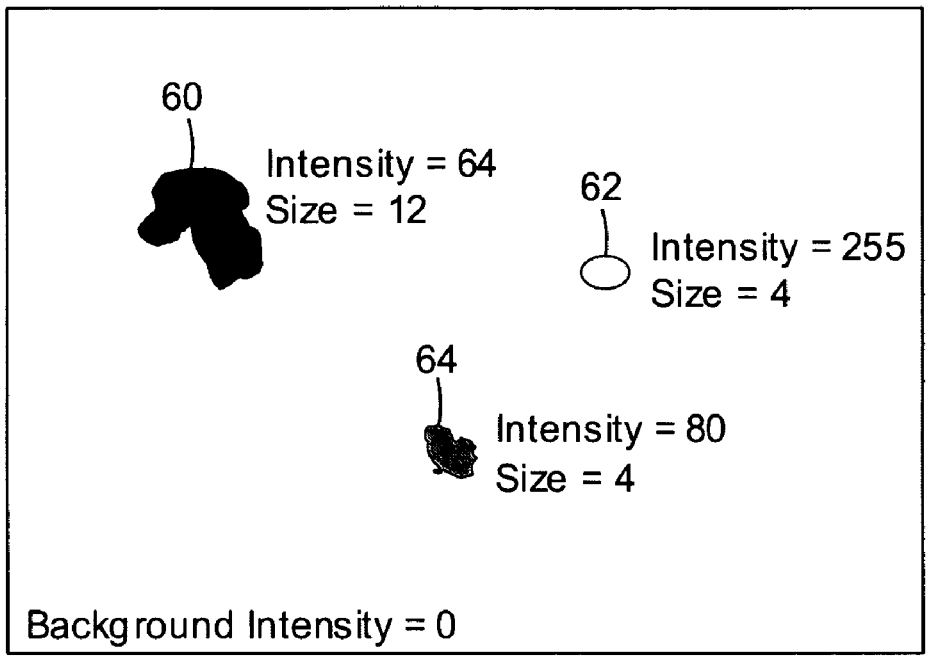
FIGS. 4a and 4b are illustrations of example images of a portion of a web used in practicing the present invention.

FIG. 4a shows a sample image containing three anomalies. In this example, an anomaly is considered defective if (its intensity is greater than 50 AND its size is greater than 10 pixels) OR (its intensity is greater than 190 and its size is greater than 2 pixels). Thus, in this example, Anomalies 60 and 62 are defects while anomaly 64 is not. Because this is a simple image, common defect detection could involve simple intensity thresholding and segregation based on blob size. As the table below shows, there is no combination of threshold and minimum blob size that results in the correct solution.

| Intensity Threshold | Minimum Blob Size | Identified Defects | Correct? |
|---|---|---|---|
| 50 | 6 | 60 | No |
| 50 | 2 | 60, 62, and 64 | No |
| 70 | 6 | None | No |
| 70 | 2 | 62, 64 | No |
| 90 | 6 | None | No |
| 90 | 2 | 62 | No |

In accordance with the present invention, anomaly images are available to multiple image processing algorithms whose combination determines the resultant defect set. An example is illustrated in the following.

| Intensity Threshold | Minimum Blob Size | Identified Defects | Correct? |
|---|---|---|---|
| 50 | 6 | 60 | |
| 90 | 2 | 62 | |
| Combination (OR) | | 60 and 62 | Yes |

The art attempts to solve this type of situation by including crude intensity information along with blob features to be used for classification. One such feature that is commonly used is the maximum pixel value within a blob. If this information is included for each anomaly, then one can correctly identify each defect as shown in the following table. One would perform a threshold of 50 to the entire image and then categorize defects using the blob size and maximum pixel intensity. In fact, for FIG. 4a, the correct solution is produced with this standard technique. The table below shows this result.

| Anomaly | Minimum Blob Size | Max Pixel Intensity | Identified Defect? | Correct? |
|---|---|---|---|---|
| 60 | 12 | 64 | Yes | Yes |
| 64 | 4 | 80 | No | Yes |
| 62 | 4 | 255 | Yes | Yes |

Figure 4B:
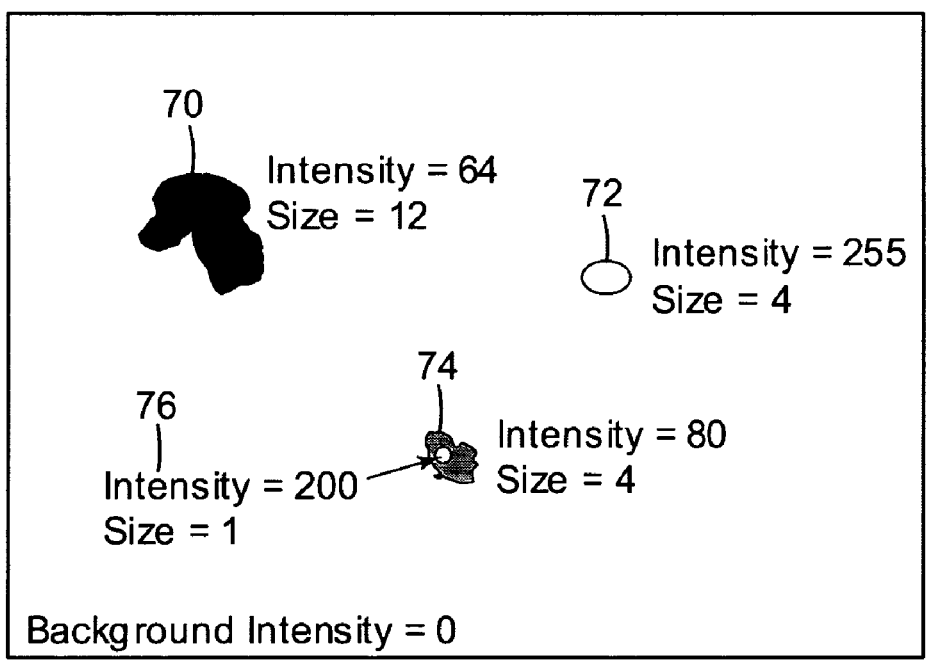

Unfortunately, actual production operations are not nearly as simple as FIG. 4a. The overwhelming majority of anomalies consist of a wide range of intensity values ranging from the background level to their maximum intensity value, sometimes with very disjointed ranges. Now, consider FIG. 4b. Anomalies 70 and 72 are similar to Anomalies 60 and 62 in FIG. 4a, respectively, but now Anomaly 74 contains a single embedded pixel 76 of intensity 200. This small, but realistic change renders known defect classification inherently innacurate. If the same intensity threshold of 50 and defect classification using the maximum pixel intensity within each anomaly are applied, the result is that Anomaly 74, which is not defective, is inaccurately classified as a defect. The table below describes this situation.

| Anomaly | Minimum Blob Size | Max Pixel Intensity | Identified Defect? | Correct? |
|---|---|---|---|---|
| 70 | 12 | 64 | Yes | Yes |
| 74 | 4 | 200 | Yes | No |
| 72 | 4 | 255 | Yes | Yes |

Again, applying the new invention results in the correct answer as shown below.

| Intensity Threshold | Minimum Blob Size | Identified Defects | Correct? |
|---|---|---|---|
| 50 | 6 | 70 | |
| 90 | 2 | 72 | |
| Combination (OR) | | 70 and 72 | Yes |

This example used a very simple image and simple detection algorithms. However, the invention is not limited to this type of image processing or defect detection. Arbitrarily complex image processing and defect extraction could be used for each detection algorithm along with complex result combination mechanisms resulting in extremely powerful defect detection for web inspection systems.

Various modifications and alterations of the present invention will be apparent to those skilled in the art without departing from the scope and spirit of this invention, and it should be understood that this invention is not limited to the illustrative embodiments set forth herein.

What is claimed is:

1. A method of inspecting a continuously moving web, comprising:

imaging a sequential portion of the continuously moving web to provide digital information, processing the digital information with at least one initial algorithm to identify regions on the web containing anomalies, extracting identified regions from the digital information, wherein the extracted identified regions represent a portion of the digital information, and analyzing the extracted identified regions with at least one subsequent algorithm to determine which anomalies represent actual defects in the moving web.

2. The method according to claim 1 further comprising storing or buffering the identified regions prior to analyzing.

3. The method according to claim 2 wherein the stored or buffered information is analyzed after the imaging has been performed on the entire web.

4. The method according to claim 1 wherein the initial algorithm comprises thresholding the digital infomation and forming a blob list.

5. The method according to claim 1 wherein the at least one subsequent algorithm includes neighborhood averaging, neighborhood ranking, contrast expansion, various monadic and dyadic image manipulations, digital filtering, texture analysis, fractal analysis, frequency processing, convolutions, morphological processing, thresholding, connected component analyses, blob processing, blob classifications, or combinations thereof.

6. The method according to claim 1 wherein the continuously moving web is normally unpatterned.

7. The method according to claim 1 wherein the continuously moving web has a pattern, and wherein the initial algorithm used to process the digital infomation is capable of distinguishing between regions of the web containing perfect pattern from regions of the web containing pattern and also possible defects.

8. The method according to claim 1, wherein the at least one subsequent algorithm characterizes at least a portion of the web into quality classifications.

9. A method according to claim 1, wherein the identified regions contain infomation, as indicated by size, having at least an order of magnitude less than the digital information.

10. The method according to claim 1, wherein the subsequent algorithm includes a plurality of steps, wherein each of the plurality of steps comprises comparing each anomaly against a combination threshold-pixel size criterion.

11. The method according to claim 10, wherein an anomaly is identified as an actual defect if any one of the criteria is satisfied.

12. The method according to claim 1, wherein at least some anomalies are reported in real time for process monitoring, process control or both.

13. A method of inspecting a continuously moving web, comprising:

imaging a sequential portion of the continuously moving optical film web to provide digital information, processing the digital information with an initial algorithm consisting of an intensity threshold followed by defect sorting based on blob size to identify regions on the web containing anomalies, extracting subimages from the identified regions in the digital information, and analyzing the extracted anomalies with the following subsequent algorithms to determine which anomalies represent actual defects in the moving web, wherein each of the subsequent algorithms consists of an intensity threshold followed by defect sorting on blob size such that for each subsequent algorithm, the intensity threshold increases as the minimum blob size decreases.

14. A method of inspecting a web, comprising:

imaging a sequential portion of the web to provide digital information, processing the digital information with at least one initial algorithm to identity regions on the web containing anomalies, extracting identified regions from the digital information, wherein the extracted identified regions represent a portion of the digital information, and analyzing the extracted identified regions with at least one subsequent algorithm to determine which anomalies represent actual defects in the web.

15. An apparatus for inspecting a continuously moving web, comprising:

an imaging device for imaging a sequential portion of the continuously moving web to provide digital information, and computational equipment for processing the digital information with an initial algorithm to identity regions on the web containing anomalies, then extracting identified regions as subimages of the digital information and then analyzing the extracted identified regions with at least one subsequent algorithm to determine which anomalies represent actual defects in the moving web.

* * * * *

UNITED STATES PATENT AND TRADEMARK OFFICE
CERTIFICATE OF CORRECTION

PATENT NO. : 7,027,934 B2  
DATED : April 11, 2006  
INVENTOR(S) : Skeps, Carl J.

It is certified that error appears in the above-identified patent and that said Letters Patent is hereby corrected as shown below:

<u>Title page,</u>  
Item [56], References Cited, OTHER PUBLICATIONS, delete "1999" and insert -- 1999, --;

<u>Column 3,</u>  
Line 8, delete "nndefined" and insert -- defined --;  
Line 21, delete "severity." and insert -- severity; --;

<u>Column 8,</u>  
Line 27, delete "innacurate." and insert -- inaccurate. --;  
Line 30, delete "defective,is" and insert -- defective, is --;

<u>Column 9,</u>  
Lines 18 and 32, delete "infomation" and insert -- information --;  
Line 40, delete "infomation," and insert -- information, --;

<u>Column 10,</u>  
Lines 26 and 41, delete "identity" and insert -- identify --.

Signed and Sealed this

Sixth Day of June, 2006

JON W. DUDAS  
*Director of the United States Patent and Trademark Office*